United States Patent [19]

Kaminer

[11] Patent Number: 5,204,264

[45] Date of Patent: Apr. 20, 1993

[54] METHOD FOR VALIDATION OF CALIBRATION STANDARDS IN AN AUTOMATIC CHEMICAL ANALYZER

[75] Inventor: Jon J. Kaminer, Richmond, Va.

[73] Assignee: E. I. Du Pont de Nemours and Company, Wilmington, Del.

[21] Appl. No.: 669,654

[22] Filed: Mar. 14, 1991

[51] Int. Cl.$^5$ .................... G01N 31/00; G01N 35/00; G01C 17/38

[52] U.S. Cl. .......................................... 436/8; 436/19; 436/43; 73/1 R

[58] Field of Search ................... 436/8, 19, 43; 73/1 R

[56] References Cited

U.S. PATENT DOCUMENTS 4,043,756 8/1977 Sommervold .......................... 436/43
4,290,775 9/1981 Stevens et al. ..................... 23/230 R

FOREIGN PATENT DOCUMENTS 62-144071 6/1987 Japan.
63-58164 3/1988 Japan.

OTHER PUBLICATIONS

Fisher '88 Catalog, p. 1337.

Primary Examiner—James C. Housel
Assistant Examiner—N. Bhat

[57] ABSTRACT

In an automated analyzer that measures concentration of samples by comparing changes in a detector response caused by said samples to a calibration curve or factor based on one or more different calibration standards stored in the analyzer, a replacement calibration standard is validated automatically by processing a portion of said replacement calibration standard as a sample prior to accepting the new calibration standard as a valid standard.

1 Claim, 5 Drawing Sheets

METHOD FOR VALIDATION OF CALIBRATION STANDARDS IN AN AUTOMATIC CHEMICAL ANALYZER

BACKGROUND OF THE INVENTION

This invention relates to a calibration standard for an automated analyzer and, more particularly, it relates to a method for validating a replacement calibration standard for an analyzer.

Many analyzers, such as on-line automatic titration instruments, rely upon the use of on-line calibration standards. The response of the instrument to the calibration standard establishes a relationship known as a calibration curve. It is assumed that a given calibration standard is stable with time and the instrumental response to the standard is a true function of the analyzer's inherent behavior. Typically a calibration standard with a known concentration is available for routine on-line checking of the instrument's response to the standard. This can be done without human intervention by many analyzers as long as there is a sufficient quantity of the calibration standard.

At times, a calibration standard is consumed or a need otherwise arises to change the standard. When this happens, one or more new calibration standards are installed in the analyzer. The new calibration standards have known concentrations which, for example, are entered by human operators into the instrument. A fault can occur if the operator enters a calibration standard concentration incorrectly or if the standard itself has an incorrect concentration label. In the case where the on-line analyzer is used to provide information which is used directly in closed-loop control of production, an off-standard product could result from such a fault. Therefore, there is value in performing a validity check on calibration standards at the time when they are changed in an automatic analyzer.

SUMMARY OF THE INVENTION

An automatic analyzer functions with the aid of a programmable computer which embodies software allowing the generation of calibration curves from calibration standards. When a new standard is installed, it is treated as an ordinary analytical sample to determine its concentration by using the system software.

The response of the analyzer to the new standard is then evaluated to confirm that it falls within some expected range of concentration (which is programmed into the analyzer). If the expected range criterion is not met by a calibration standard, the analyzer does not update the calibration curve and sends an error message or alarm. Pending intervention by the operator, the analyzer may either continue to rely on the calibration curve last determined or cease analysis and go into a standby mode.

DETAILED DESCRIPTION OF THE PREFERRED EMBODIMENT

Figure 1:
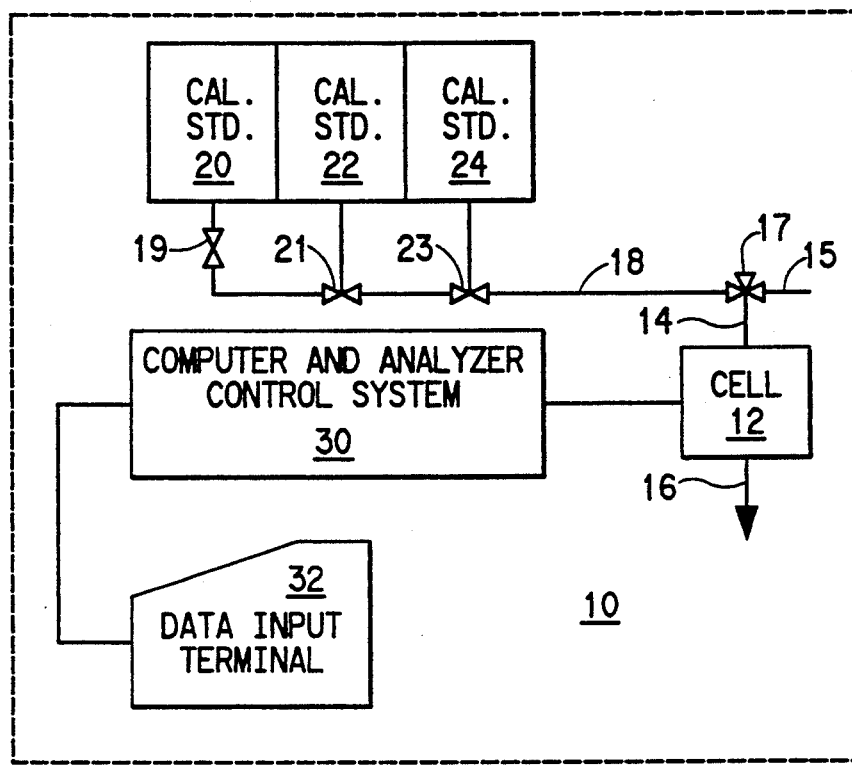
FIG. 1 is a schematic diagram representing an instrument analyzer used in performing the invention.
Figure 2:
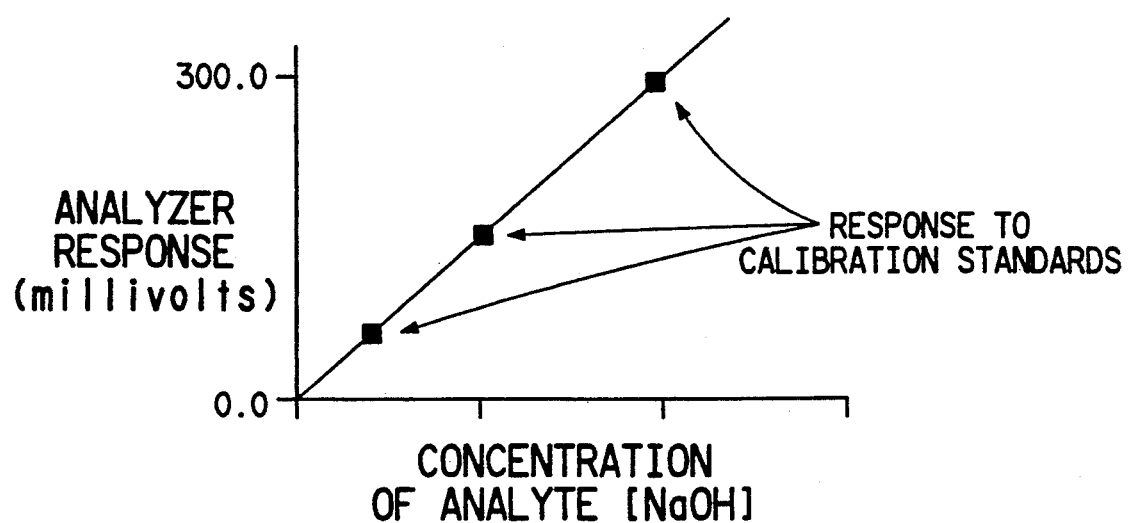
FIG. 2 is a schematic of a calibration curve for the instrument of FIG. 1.
Figure 3A:
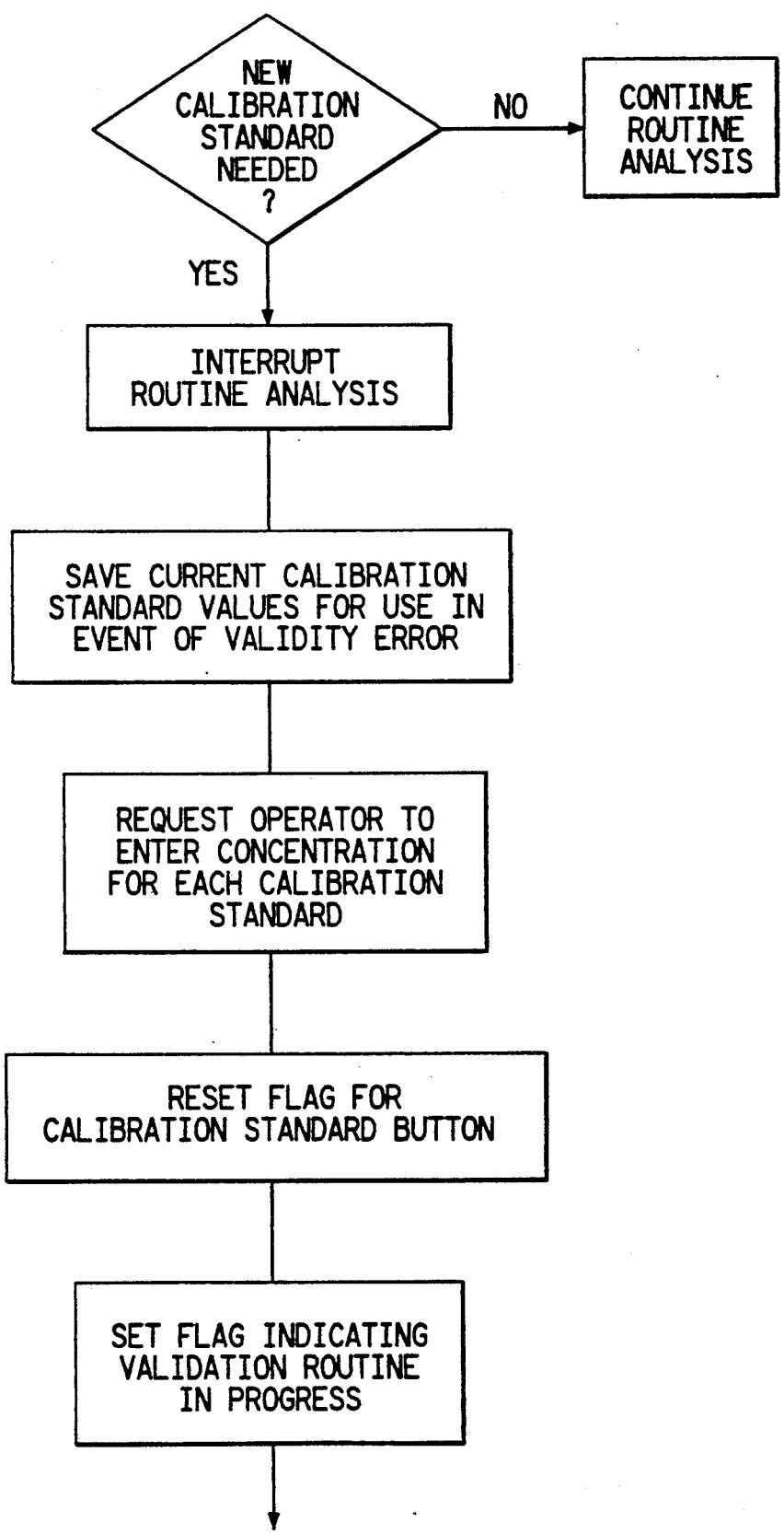
FIGS. 3a-3d are logic flow diagrams of the program steps to operate the computer of FIG. 1 for validating calibration.
Figure 3B:
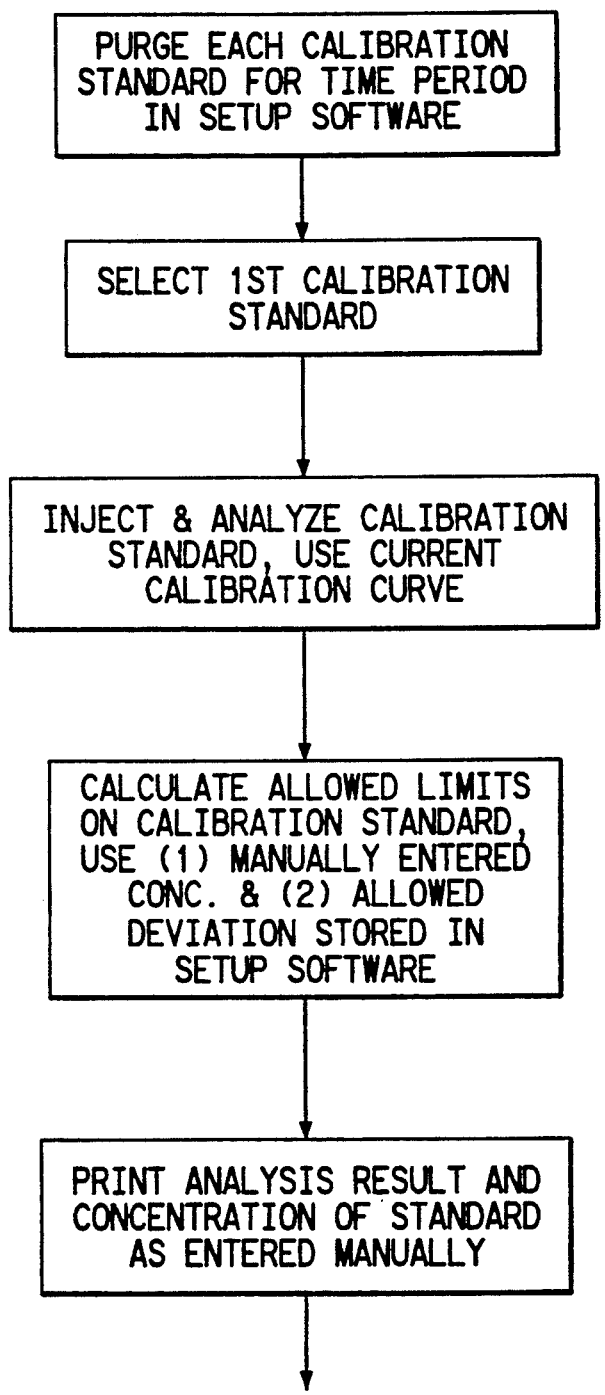
Figure 3C:
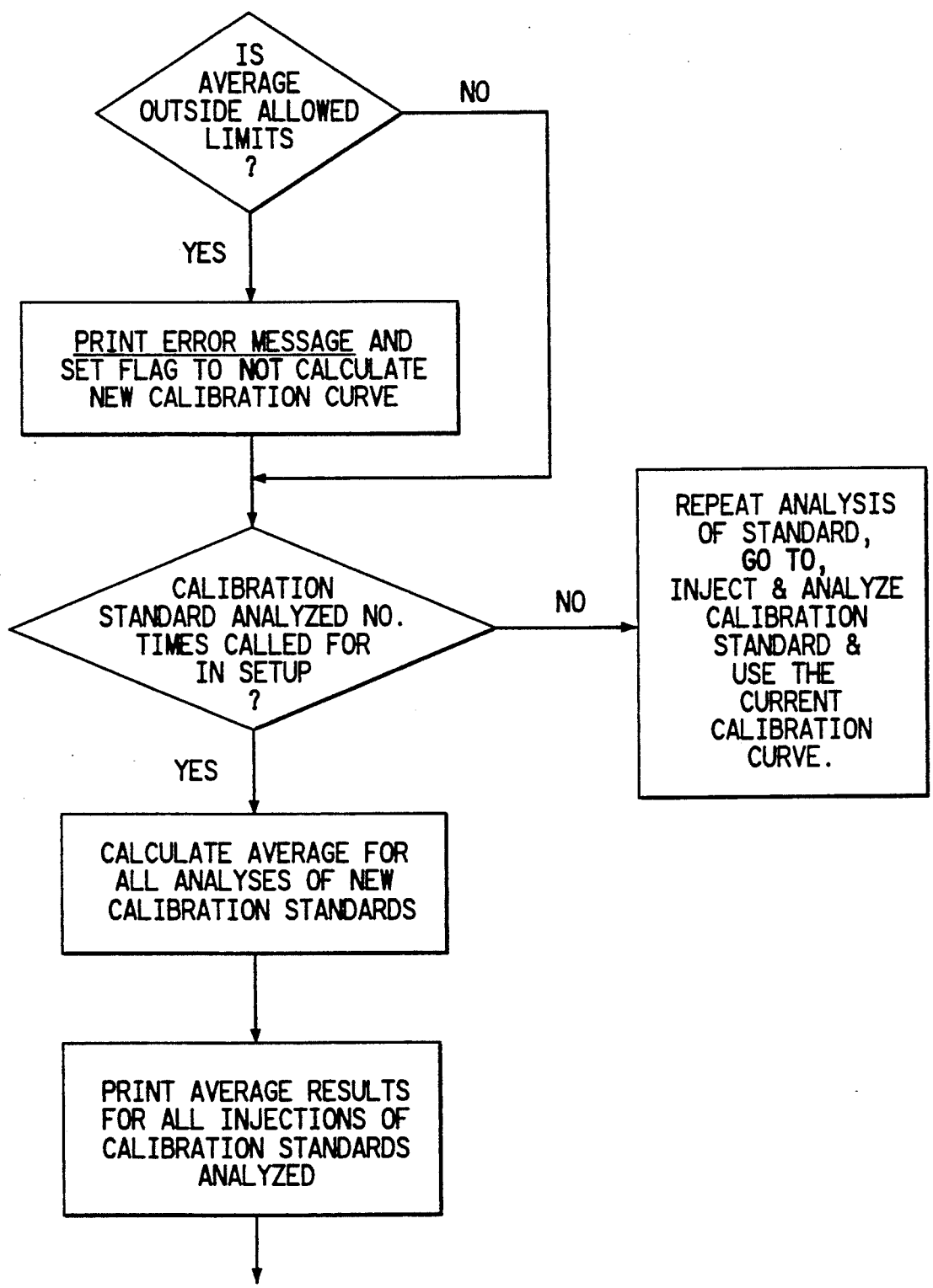
Figure 3D:
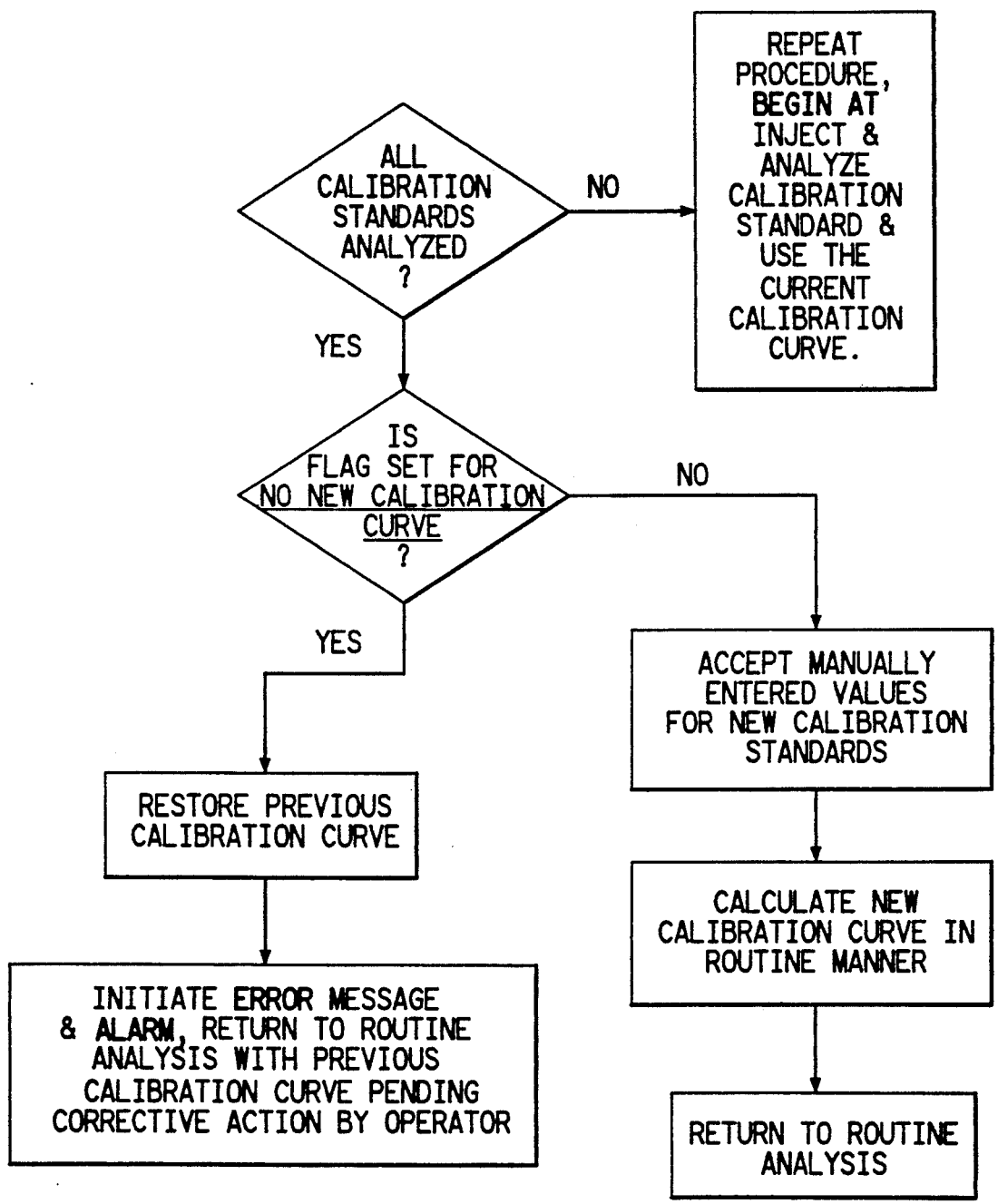

Referring now to FIG. 1, the instrument 10 includes a sample flow analysis cell 12 having an inlet 14 and an outlet 16. A header pipe 18 connected to calibration standard cells 20, 22, 24 is connected to inlet 14. A computer and analyzer control system 30 is coupled between a data input terminal 32 and sample flow analysis cell 12. Preferably, the instrument is a FIAtron Process Flow Injection Analyzer for determining total alkalinity in water (Eppendorf, N. A., 545 Science Drive, Madison, Wis. 53719). The general operation of a flow injection analyzer (FIA) is disclosed in U.S. Pat. No. 4,290,775 assigned to Dow Chemical Company. The FIA determines the concentration of analyte in a sample in the following way. First, a known amount of sample is injected into a flowing stream or "carrier" which is continuously supplied to the FIA. The carrier produces a known and reproducible response in a detection device, which might be ionic conductivity, specific ion electrodes or a spectrometric means. Any changes detected in the characteristics of the carrier (e.g. ionic conductivity or ion specific electrode or spectral absorbance responses) may be directly related to the concentration of the species to be analyzed in unknown samples. Typically, the response of the detector is then compared to the response of a series of standard samples which have a known concentration. The process of generating a calibration curve is used to calibrate the response of the analyzer detector to a series of standard calibration samples. Each standard has a known concentration of the analyte and the span in range of concentration of the standards includes the expected concentration in the test sample of unknown concentration. A graphical representation of detected analyte characteristic response versus the known concentration of analyte in the standard samples, the calibration curve, is illustrated in FIG. 2.

In this example a micro-processer controlled FIA is used to monitor process streams and can provide information to assist in control of the processes. Here the total alkalinity (KOH, NaOH, $Na_2CO_3$, $NaHCO_3$, $K_2CO_3$, $KHCO_3$) of a process stream is sought. A solution containing a pH buffer (which is prepared to be acidic) and a pH color indicator (methyl orange) is used as the carrier and a colorimeter (which determines the absorbance of the carrier at about 510 nanometers) is used as a detector. At start-up of the FIA, a calibration curve is derived by analyzing calibration standard samples, 20, 22 and 24 in FIG. 1, sequentially in the FIA. Standards 20, 22 and 24 are prepared to contain three different levels of alkalinity which span the expected range of process stream samples. Each standard solution may be analyzed in turn by operating selection valve 19 in the case of standard 20 or valve 21 in the case of standard solution 22 and so forth, while selection valve 17 is in position to receive any one of the standard solutions. Following the calibration of the FIA, a calibration curve like FIG. 2 is stored electronically in the machine's memory. Any sample of unknown concentration within the concentration span of the calibration curve, FIG. 2, may then be introduced to the analysis cell 12 via inlet tube 15, while selection valve 17 is positioned to receive an analytical sample through tube 15. The process samples are analyzed and the concentration determined by comparting the detector response to the calibration curve, FIG. 2, in the machine's memory.

The micro-processer controlled FIA calls for additional calibrations to be run periodically to correct for any drift in FIA response (when a significant drift is found, an alarm signal is initiated). As a result of running periodic calibrations, the calibration solutions eventually are used up and must be resupplied. When this resupply is done, it is necessary to manually enter the concentration of the new calibration standard in the software so that the micro-processor will be able to determine a new calibration curve. This invention is used here to prevent an incorrect standard concentration manual entry from causing an incorrect calibration curve to be determined. New standard solution(s) (any one or all of 20, 22 and 24) is placed in the appropriate standard container which is connected through valves 19, 21 and 23 to the FIA. As shown in FIGS. 3a-3d, a manual command is given to the FIA and the operator interface display shows the currently entered concentration of the first standard. If this standard concentration has been changed, a second manual command to FIA is made to enter the new standard concentration. If the concentration has not been changed, a manual command to continue is given. The FIA operator interface displays the currently entered concentration of the second standard. Again, a manual entry of a new concentration or a command to continue is given. The same sequence of commands is followed for the third standard concentration. The manual command to start analysis causes the FIA to inject a calibration standard and analyze each standard solution as if it were running a sample but using the old calibration curve stored in memory and based on the standard solutions previously used and now exhausted. This old calibration curve is retained in the memory and used to calculate the concentration of each of the calibration solutions replaced. The calculated values are then compared to the numbers just manually entered for the new solutions. If for each of the three standards the two values are within a predetermined differential of each other (e.g. 3 parts per thousand), the entered value is accepted as the true value and is used in determining a new calibration curve. If any of the calculated and entered values fail to agree within the predetermined differential, an error signal is initiated and the calibration curve is not updated in the FIA's memory. Therefore, the analyzer confirms that the correct concentration for the standard was known and entered, and that no upsets were introduced during the standard solution change which could have temporarily altered the response of the analyzer.

The method of this invention is also applicable to the calibration of an automated analyzer employing a single calibration standard. In this case, the response of the analyzer to the analyte is assumed to be proportional throughout a range of concentration. Hence, a linear calibration factor can be computed to determine the concentration of any analytical sample from the analyzer's response. In practice, a single calibration standard is used to check the response of the analyzer. For example, a calibration standard of X concentration units (e.g. grams of standard per milliliter of solution) may have a response of Y millivolts. Therefore, a calibration factor equal to the ratio X/Y is calculated and stored in the analyzer. A sample of unknown concentration is then submitted for analysis by the analyzer and a response of Z millivolts is obtained. The analyzer then computes the concentration of sample as the product of the internal calibration factor and analyzer response to the sample, i.e. the sample concentration is Z(X/Y). This invention may be used to confirm that the concentration of the single calibration standard used was correct and that no upsets to the normal operation of the analyzer operation occurred as a result of renewing the supply of the single calibration standard solution.

What is claimed is:

1. In a method for analyzing the concentration of a sample using an automatic analyzer wherein the possibility of human operator faults in entry of calibration standard concentrations or mislabeled standards exists that includes the steps of generating a calibration curve by means of said automated analyzer based on the concentrations of one or more calibration standards coupled to said automated analyzer and storing said curve in said analyzer, each of said calibration standards having a different known concentration, detecting a change in response caused by the concentration of said sample and comparing said change to said calibration curve to determine if said concentration of said sample is within a predetermined range of said calibration curve, the improvement being validating the concentration of a replacement calibration standard to be used in place of an expended calibration standard in said analyzer, said improvement comprising: using a portion of said replacement calibration standard as a sample, comparing said concentration of said portion to said calibration curve and signaling if said concentration of said portion is not within said predetermined range.

* * * * *